(12) United States Patent
Bjornson et al.

(10) Patent No.: US 8,252,911 B2
(45) Date of Patent: Aug. 28, 2012

(54) COMPOSITIONS AND METHODS FOR USE IN ANALYTICAL REACTIONS

(75) Inventors: Keith Bjornson, Newark, CA (US);
Arek Bibillo, Cupertino, CA (US);
Lubomir Sebo, Redwood City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 320 days.

(21) Appl. No.: 12/370,472

(22) Filed: Feb. 12, 2009

(65) Prior Publication Data

US 2009/0208961 A1 Aug. 20, 2009

Related U.S. Application Data

(60) Provisional application No. 61/065,439, filed on Feb. 12, 2008.

(51) Int. Cl.
*C07H 21/02* (2006.01)
*C12Q 1/68* (2006.01)
*C07H 21/04* (2006.01)

(52) U.S. Cl. .................... 536/22.1; 435/6.12; 536/24.33

(58) Field of Classification Search ............. 435/6, 91.2; 536/24.33

See application file for complete search history.

(56) References Cited

U.S. PATENT DOCUMENTS

| 5,547,839 | A | 8/1996 | Dower |
| 6,210,896 | B1 | 4/2001 | Chan |
| 6,232,075 | B1 | 5/2001 | Williams |
| 6,255,083 | B1 | 7/2001 | Williams |
| 6,610,486 | B1 | 8/2003 | Dahlhauser |
| 6,762,048 | B2 | 7/2004 | Williams |
| 6,787,308 | B2 | 9/2004 | Balasubramanian |
| 6,803,201 | B2 | 10/2004 | Sorge et al. |
| 6,917,726 | B2 | 7/2005 | Levene |
| 6,936,702 | B2 | 8/2005 | Williams |
| 7,041,812 | B2 | 5/2006 | Kumar |
| 7,056,661 | B2 | 6/2006 | Korlach |
| 7,482,120 | B2 | 1/2009 | Buzby |
| 7,491,498 | B2 | 2/2009 | Lapidus |
| 2003/0096253 | A1 | 5/2003 | Nelson |
| 2003/0190647 | A1 | 10/2003 | Odera |
| 2003/0215862 | A1 | 11/2003 | Parce |
| 2004/0048300 | A1 | 3/2004 | Sood |
| 2004/0152119 | A1 | 8/2004 | Sood |
| 2004/0224319 | A1 | 11/2004 | Sood |
| 2006/0194232 | A1 | 8/2006 | Turner et al. |
| 2007/0036511 | A1 | 2/2007 | Lundquist |
| 2007/0072196 | A1 | 3/2007 | Xu et al. |
| 2007/0077564 | A1 | 4/2007 | Roitman |
| 2007/0188750 | A1 | 8/2007 | Lundquist |
| 2007/0206187 | A1 | 9/2007 | Lundquist |
| 2008/0030628 | A1 | 2/2008 | Lundquist |
| 2008/0299565 | A1 | 12/2008 | Schneider |

FOREIGN PATENT DOCUMENTS

| WO | WO 91/06678 | 5/1991 |
| WO | WO 96/27025 | 9/1996 |
| WO | WO 99/05315 | 4/1999 |
| WO | WO 2004074503 A2 * | 9/2004 |
| WO | 2006/086673 A2 | 8/2006 |
| WO | WO 2006086673 A2 * | 8/2006 |
| WO | WO 2007/123763 | 11/2007 |

OTHER PUBLICATIONS

International Search Report and Written Opinion dated Oct. 7, 2009 for related PCT case, PCT/US2009/000921.
International Preliminary Report on Patentability dated Aug. 26, 2010 for related PCT case, PCT/US2009/000921.
Extended Search Report dated Apr. 18, 2011 from related EP 09711261.9.
U.S. Appl. No. 61/026,992, Otto.
Di Mascio, et al., Biochem Soc Trans. Dec. 1990; 18(6): 1054-6.
Eid et al., Science 323:133-138 (Jan. 2, 2009).
Korlach et al., PNAS U.S.A. 105(4): 1176-1181. (2008).
Levene, et al. Science 299:682-686, Jan. 2003.
Lundquist et al., Optics Letters, vol. 33, Issue 9, pp. 1026-1028, 2008.
Stahl, et al., Carcinogenesis vol. 18 No. 1 pp. 89-92, 1997.

\* cited by examiner

*Primary Examiner* — Prabha Chunduru
(74) *Attorney, Agent, or Firm* — Robert H. Reamey

(57) ABSTRACT

Compositions, methods, substrates and systems for use in analysis of single molecule reactions and particularly single molecule nucleic acid sequence analysis. Compositions that include non-reactive, distinguishable or undetectable competitive substrates for the reaction system of interest are provided, as well as their use in systems and substrates for such applications, such compounds typically preferably polyphosphate chains or analogous structures.

21 Claims, 6 Drawing Sheets

COMPOSITIONS AND METHODS FOR USE IN ANALYTICAL REACTIONS

CROSS-REFERENCE TO RELATED APPLICATIONS

This application claims priority to Provisional U.S. Patent Application No. 61/065,439, filed Feb. 12, 2008, the fill disclosure of which is hereby incorporated herein by reference in its entirety for all purposes.

STATEMENT REGARDING FEDERALLY SPONSORED RESEARCH

Not Applicable.

BACKGROUND OF THE INVENTION

Methods of determining the sequence of nucleotides in nucleic acids have undergone substantial changes from the original adoption of gel-based Sanger sequencing, through four color capillary electrophoresis based approaches, both of which relied upon the electrophoretic separation of nested synthesis fragment sets to identify sequentially terminated synthesis products, and as a result, identify each successive base in the sequence. Newer approaches to sequencing rely upon "sequencing by incorporation" where each base is identified sequentially, as it is added in a primer extension reaction. These range from pyrosequencing and other related methods that add a single base at each step and look to see if it was incorporated, to processes that add multiple different types of nucleotides each labeled with a different fluorescent dye, and identify which base was incorporated based upon the dye incorporated at any given step. Typically, such processes require an iterative or step by step process that employs nucleotides that include extension terminating groups, such that after a single incorporation event, no new bases are added until the added base can be identified. The terminating group is then removed and the next extension step is allowed to proceed.

In still more elegant methods, individual molecular complexes are observed in real time, as they incorporate labeled nucleotides. The incorporation event provides a characteristic optical signal that, along with a spectrally distinct dye, identifies both the incorporation event and the type of base incorporated. In such methods, the labeling group is often provided coupled to the phosphate chain of the nucleotide analog beyond the alpha phosphate, resulting in cleavage of the label from the nucleotide upon incorporation. This allows both the synthesis of an entirely native strand of nucleic acid, and the release of a labeling group that might otherwise confound the observation and analysis.

The present invention provides improved compositions, methods and systems for performing single molecule real time analyses, and particularly single molecule, real time nucleic acid sequence analysis.

BRIEF SUMMARY OF THE INVENTION

The present invention provides compositions, substrates, methods, and systems that employ competitive, but otherwise unreactive substrates or inhibitors in analytical reactions to modulate the rate of reaction of these systems. In particular, the present invention is directed to the real time analysis of single molecule (or single complex) reactions, which employ competitively inhibiting compositions in conjunction with the reactants for the monitored reaction. The presence of such competitors provides a mechanism for modulating the rate of the monitored reaction to provide numerous advantages. In a particularly preferred aspect, polymerase mediated, template dependent nucleic acid synthesis is modulated in accordance with the invention by providing within the reaction mixture competitive inhibitors to the polymerase binding of incorporatable nucleoside polyphosphates, that are also present in the mixture. Such competitors are characterized by their ability to competitively and reversibly associate with the polymerase, with respect to such nucleoside polyphosphates, and also their inability to be incorporated into the synthetic reaction.

Particularly preferred is the use of unincorporatable nucleotide analogs that are either unlabeled, or distinctively labeled, in the analysis of polymerase mediated, template dependent nucleic acid synthesis and sequence characterization.

Thus, in at least one aspect, the invention provides compositions, comprising a complex comprising a nucleic acid polymerase, a template sequence and a primer sequence complementary to at least a portion of the template sequence. Also included is at least a first type of incorporatable labeled nucleotide analog, and at least a first type of unincorporatable competitive polymerase reagent, said unincorporatable competitive polymerase reagent being either unlabeled or differentially labeled from the incorporatable labeled nucleotide analogs.

Relatedly, the invention also provides methods of determining nucleotide sequence information from a target nucleic acid sequence. The methods comprise providing the target nucleic acid sequence in a complex with a primer sequence complementary to at least a portion of the target nucleic acid sequence, and a nucleic acid polymerase enzyme capable of extending the primer sequence in a target sequence dependent manner. The complex is contacted with a mixture of labeled incorporatable nucleotide analogs and at least a first unincorporatable competitive polymerase reagent that is either unlabeled or differentially labeled from the incorporatable nucleotide analogs. Target dependent incorporation of an incorporatable nucleotide analog is then detected to identify a nucleotide in the target nucleic acid sequence.

DETAILED DESCRIPTION OF THE INVENTION

I. General

Figure 1:
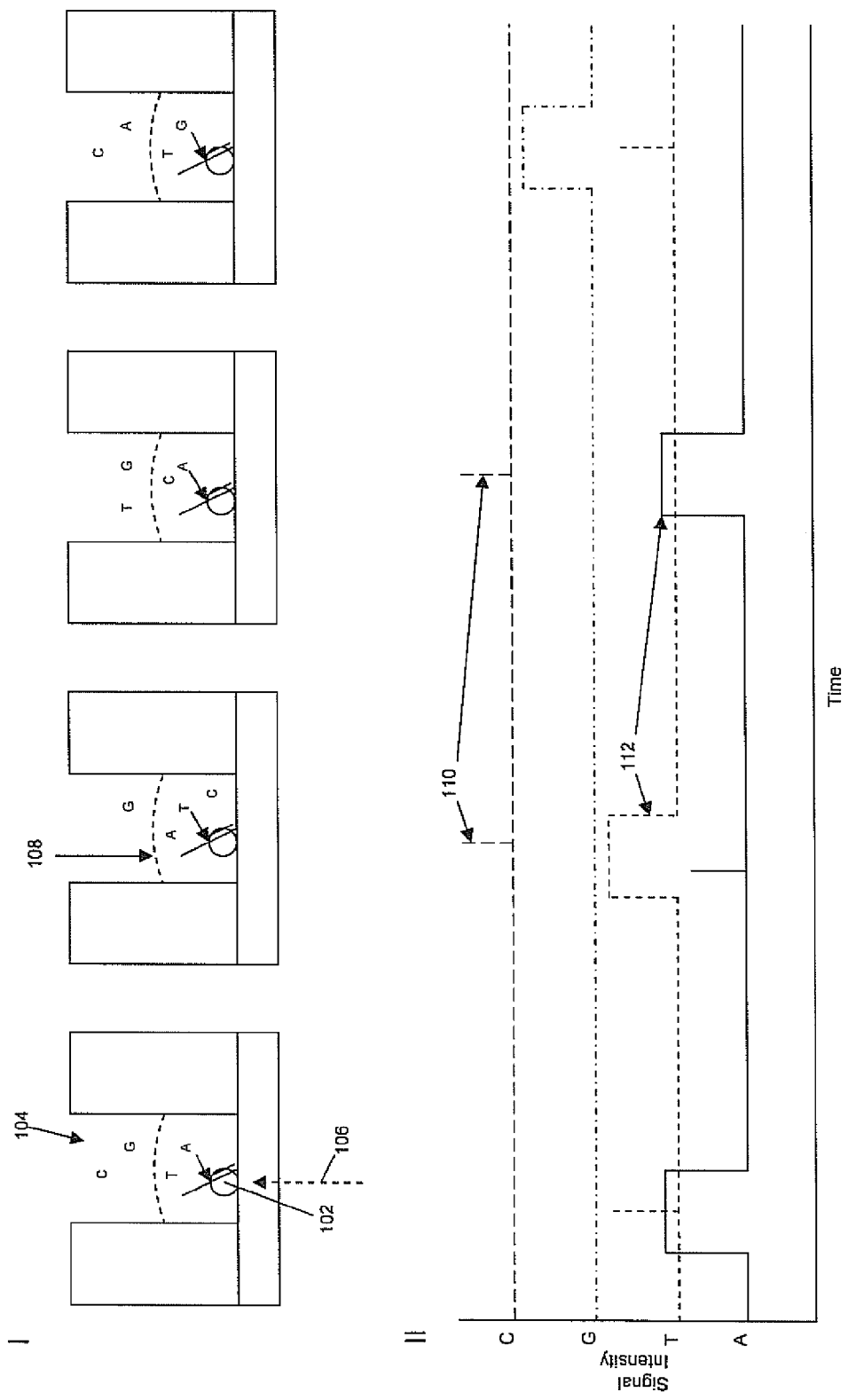
FIG. 1 schematically illustrates an exemplary single molecule real time analysis of nucleic acid synthesis.

The present invention generally provides methods, compositions and systems for improved real-time analyses and particularly nucleic acid sequence analyses. In particular, the invention provides methods and compositions for use in single molecule analysis of a desired reaction, where the reaction rate is modulated through the presence of one or more competitive inhibitors of the reaction of interest. In particular, the invention includes the use of reagents that reversibly associate with one or more components of the reaction of interest to compete with the normal progression of that reaction, in order to modulate the progression of that reaction. By way of example, non-reactive, non-indicative reagent surrogates are included in the reaction mixture along with the labeled reagents themselves, in order to reduce the likelihood of observing non-specific events that are not necessarily associated with the reaction that was to be observed, as well as provide other advantages to such systems. Modulation of the concentration of these compounds within the reaction mixture allows for the modulation of the rate of the reaction, providing ability to improve detection of the reaction of interest, enhance stringency of such reactions, and the like.

In one preferred context, the invention is directed to compositions for use in real-time nucleic acid analysis that employ competitive reagents to nucleoside polyphosphates, in order to modulate the rate of polymerase mediated nucleic acid synthesis. In this context, the compositions of the invention will typically include, in addition to labeled nucleotide analogs, surrogate or inhibitor compounds that are capable of reversibly associating with the polymerase enzyme in a manner that is competitive to the incorporatable nucleoside polyphosphate compounds in the reaction mixture. These surrogate compounds cannot be incorporated in a primer extension reaction, and are either unlabeled, or are labeled in a fashion that allows for their ready distinction from those labeled nucleotides or nucleotide analogs that can be incorporated. Such surrogate compounds typically comprise a structure that is mimetic of a nucleoside polyphosphate in its interaction with the polymerase, but is non-incorporatable.

Thus, in one aspect, the compounds used in the invention will typically comprise a polyphosphate portion that is coupled to a cyclic and/or aromatic portion that mimics the nucleoside portion of a nucleotide. In some contexts, nucleoside polyphosphates may be employed as the surrogate compounds, but in which the structure of the compound is adjusted to render it unincorporatable, or substantially unincorporatable. Such compositions are described in greater detail, below. By unincorporatable is generally meant that a given compound will either not be incorporated by a polymerase enzyme in template dependent primer extension or incorporated at such a low level, e.g., at less than 5%, preferably less than 15, and more preferably less than 0.1% of the frequency of a corresponding nucleoside polyphosphate employed in the given reaction mixture, i.e., a labeled nucleoside tri, tetra, penta, hexa or heptaphosphate.

As stated above, in particularly preferred aspects, the present invention is directed to improved methods and compositions used in performing single molecule real time nucleic acid sequencing by incorporation, also termed SMRT™ sequencing. As noted previously, SMRT™ sequencing methods typically employ a nucleic acid synthesis complex that includes a polymerase enzyme, e.g., a DNA polymerase, a template sequence, and a primer sequence that is complementary to at least a portion of the template sequence. In typical primer extension reactions, the polymerase extends the primer sequence by incorporating additional nucleotides that are complementary to the next nucleotide in the underlying template sequence. In the real-time monitoring processes used with the invention, the reaction employs four distinctively labeled nucleotides, e.g., each labeled with a distinguishable fluorescent label. The complexes are then configured such that upon incorporation of a given base, a characteristic optical signal is produced, that both signals an incorporation event and allows identification of the type of base incorporated.

In some cases, this configuration involves the immobilization of the complex within an optically confined region, such that an incorporating nucleotide is observable for a period of time that is characteristic of that incorporation. In particular, upon incorporation, a labeled nucleotide will be retained within or proximal to the active site of the enzyme. Examples of such optically confined regions include regions at or near a surface of a transparent substrate that is illuminated using total internal reflection (TIRF) spectroscopy to illuminate only species that are very close to the substrate surface. In such systems, nucleotides that are being incorporated into a complex immobilized within the illumination region at or near the surface, will be preferentially illuminated, and as a result, distinguishable over other, non-incorporated molecules. Typically, the complexes are provided in a configuration that provides for the optical resolution of individual molecular complexes, to permit single molecule (or single complex) elucidation of nucleic acid synthesis. Such single molecule configuration may include providing complexes diluted over a surface such that sufficient space is provided between the individual complexes to provide for optical resolution. Alternatively or additionally, it may comprise immobilization of individual complexes in different confined spaces, including, for example, optically confined regions as discussed below.

In other methods, the complex may be provided immobilized within an optically confined structure, such as a zero mode waveguide (ZMW). Such ZMWs provide for an illumination region that is confined in three dimensions, as opposed to only one. In particular, a nanoscale aperture is provided through a metal cladding layer that is disposed over a transparent substrate, to define the "core" of the ZMW. This nanoscale well structurally confines the illumination to the dimensions of the core. Further, where the cross sectional dimensions of the core are in the nanoscale regime of, e.g., between about 20 and about 500 nm, it will not permit passage of light of a frequency higher than a cutoff frequency from passing through the core. Instead, light illuminating one end of the core will be subject to evanescent decay through the core, resulting in a shallow illuminated region within the core, thus confining the illumination in the third dimension. By immobilizing a complex upon the transparent "floor" of the ZMW, one can selectively illuminate and observe interactions that occur at or around the complex without excessive interference from other reagents in the overall reaction mixture. The complex is then exposed to fluorescently labeled nucleotide analogs that are preferably labeled upon a phosphate group that is released upon incorporation.

One can identify the fluorescent nucleotides that are incorporated based upon their characteristic signal profile, which typically includes a longer retention time within the illumination region or volume as compared to non-incorporated molecules, and free labeled polyphosphate groups. Further, based upon the spectral characteristics of the fluorescent signal, one can then identify the type of base associated with such incorporation events. This process is schematically illustrated in FIG. 1.

As shown in FIG. 1, Panel I, a polymerase/template/primer complex 102 is provided immobilized within an illumination volume of a zero mode wave guide (ZMW) 104. Because of the dimensions of the ZMW 104, illumination directed at the ZMW from the bottom surface (shown as the dashed arrow 106), only penetrates a short distance into the ZMW, effectively illuminating only a small volume therein (as shown by the dashed line 108). As labeled nucleotides (shown as A, T, G and C) diffuse quickly in and out of the illumination volume, they are only transiently illuminated, thus yielding, at best, extremely short fluorescent signals that are detected through the bottom of the ZMW 104, shown as brief spikes 110, in the signal traces shown in Panel II, which corresponds to the schematic illustrations above the plots. When a nucleotide is incorporated by the polymerase into the growing nascent strand in primer extension, it is retained within the illumination volume for a period that exceeds transient diffusion and produces a longer fluorescent signal 112, as a result. Because each type of nucleotide bears a spectrally distinguishable label, its incorporation can be independently observed/identified (shown by the multiple traces in Panel II of FIG. 1). These characteristic signal profiles are then used to identify whether a base was incorporated and which base it was.

In still other processes, the reagents of the system are configured to provide an optical signal primarily only in the event of incorporation by the complex. For example, such systems include fluorescent energy transfer dyes that produce signal only when in proximity to one another (donor-acceptor pairs), or sufficiently separated from one another (donor-quencher pairs). For examples a donor dye may be provided coupled to the polymerase in the complex, while the acceptor is coupled to a nucleotide. Upon incorporation, the two dyes are brought into sufficient proximity to affect energy transfer and produce a characteristic signal. Conversely, one can employ a donor-quencher pair on the nucleotide, where one of the donor or quencher is provided coupled to an incorporated portion of the nucleotide, e.g., the nucleobase, while the other member of the pair is provided upon tie released phosphate groups. Upon incorporation and hydrolysis of the phosphate chain, the quenched dye diffuses sufficiently away from the quencher dye, to allow a characteristic signal indicative of incorporation. (See, e.g., U.S. Pat. No. 6,232,075, incorporated herein by reference in its entirety for all purposes).

These real time processes benefit from a number of advantages, including, for example, speed of base calling, increased read-lengths from naturally processive polymerases operating in what is closer to a natural environment, low reagent consumption, and others. Notwithstanding these advantages, there remain areas where such systems could still be improved. In particular, because the foregoing systems often rely upon the retention of the labeled nucleotide within an observation region that results from the specific interaction of the nucleotide with a polymerase enzyme, they can be adversely impacted by non-specific interactions in that same region that yield similar retention. Such interactions may include, for example, non-specific interactions between nucleotides and the polymerase enzyme, such as binding of incorrect nucleotides for the next incorporation space, surface adsorption of nucleotides on the enzyme. Alternatively or additionally, such interactions may stem from non-specific interactions between the nucleotides and other parts of the system, such as the substrate surfaces that lie within the observation region, also termed "sticking".

By way of example, in the case of nucleic acid sequencing in an optically confined region, a polymerase in the complex will randomly sample the nucleotides proximal to its active site until it finds the correct nucleotide to be incorporated in the primer extension reaction, i.e., that is complementary to the next base in the template sequence. Typically, this random sampling will occur much more rapidly than an incorporation event, and thus, will not provide a confounding signal event. However, in some cases, multiple samplings of the same type of base without incorporation, may appear similar to an incorporation event, and thus increase the possibility of an incorrect base call. This problem can be further enhanced in reaction mixtures that include relatively low concentrations of the nucleotides, as the ability for other, different nucleotides to compete out a repeatedly sampled nucleotide will be decreased, thus increasing the likelihood of repeated sampling.

In another example, a nucleotide that is not being incorporated, or even sampled by the polymerase in the complex, may nonetheless, become temporarily or permanently immobilized within the observation region, and thereby become detectable for an extended period of time that can again, provide a confounding signal, and again, a potential for an incorrect base call.

II. Competitive Substrates

The present invention addresses the issues noted above by providing compositions that include competitive reagents to the labeled reagents used in the reaction of interest, such as labeled nucleoside polyphosphates used in the polymerase mediated polymerization reaction. The use of such competitive reagents not only reduces potential for the non-specific interactions described above, but also allows for the better control of the timing and/or rate of reactions, e.g., incorporation events, to suit the needs of a particular application or system. As used herein, the phrase "competitive polymerase reagent" refers to a compound that interacts with a polymerase or polymerization complex (or component of such complex), in a competitive fashion with incorporatable nucleotide reagents, such as nucleoside polyphosphates, including for example, labeled nucleoside tetra, penta or hexaphosphates, including those that are fluorescently labeled, e.g., as described in U.S. Pat. Nos. 6,936,702, and 7,041,812. For purposes of the invention, the competitive reagents used herein exclude natural products of the reaction of interest. Thus, for example, a competitive polymerase reagent, and particularly an unincorporatable competitive polymerase reagent excludes the natural products of the incorporation of a given nucleotide or nucleotide analog into a nascent nucleic acid strand, to the extent such products may compete with the nucleotides or nucleotide analogs in association with the polymerase. For example, such competitive reagents exclude released polyphosphate components that specifically result from nucleotide or nucleotide analog incorporation by a polymerase. Notwithstanding the foregoing, in some cases, excess amounts of such polyphosphate components may be added as the competitive reagents. Such excess amounts would typically be in line with the relative concentrations set forth herein, and in such concentrations would fall within the scope if the invention, i.e., they would far exceed amounts of such compounds that result from nucleotide or nucleotide analog turnover.

In a particularly preferred aspect, the compositions of the invention incorporate, in addition to the labeled nucleotide analogs, unlabeled, or differentially labeled, and unincorporatable nucleotide analogs or compounds that mimic nucleotides or nucleotide analogs in their interaction with polymerase enzymes.

As noted previously, in accordance with the invention, the competitive nucleotide analogs or mimics thereof, are both unincorporatable by the polymerase enzyme in a primer extension reaction, and are either unlabeled or otherwise undetectable in the analytical system, or are otherwise easily distinguished from the other detectable and incorporatable nucleotide analogs that are of real interest in the analysis. For ease of discussion, these may be referred to hereafter as "unlabelled" nucleotide analogs. These unlabeled compounds compete with the labeled analogs for the non-specific interactions that can yield the problems alluded to previously.

Figure 2:
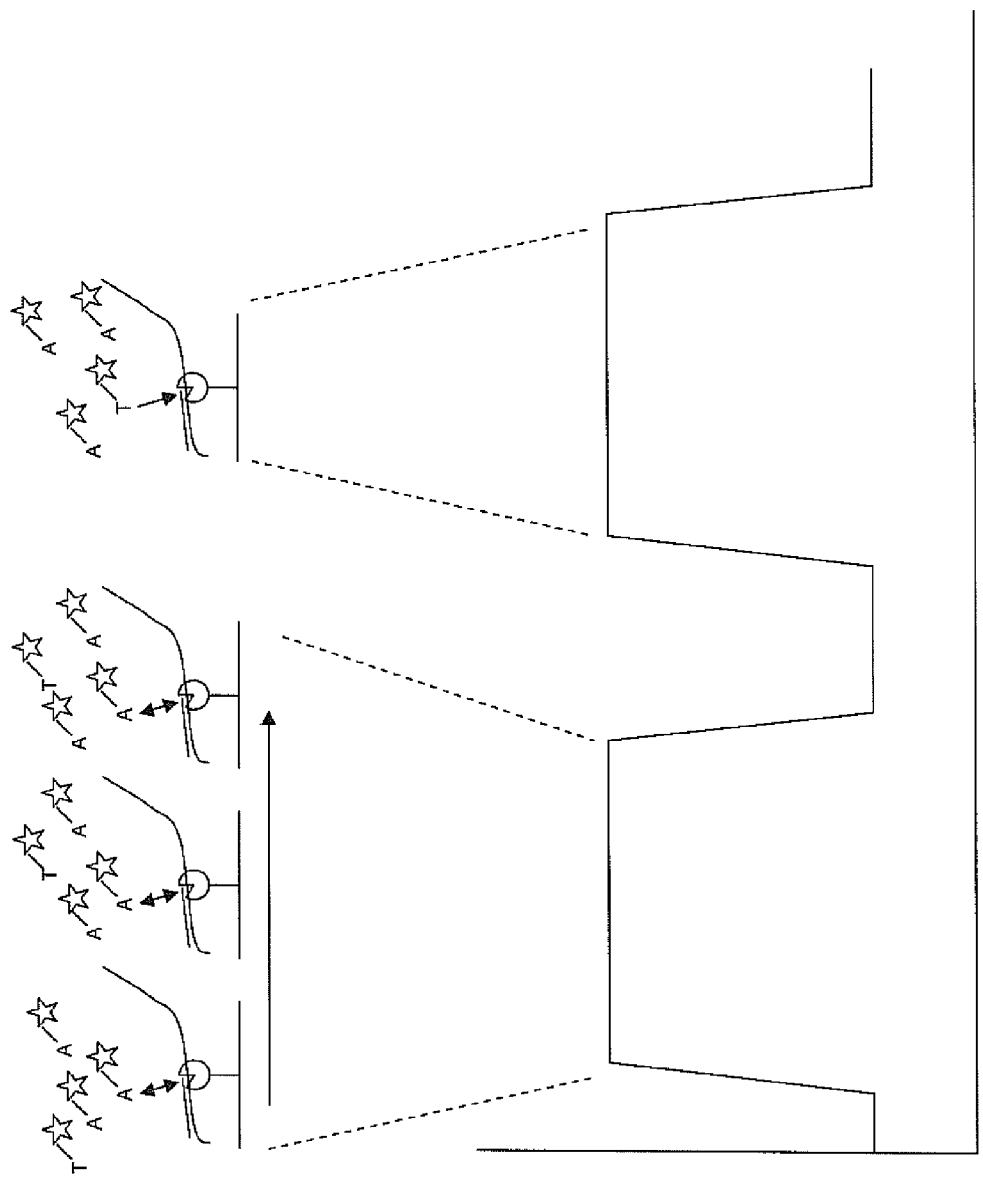
FIG. 2 schematically illustrates redundant nucleotide sampling in a nucleic acid synthesis reaction system.

For example, FIG. 2 schematically illustrates a system that repeatedly samples a given incorrect nucleotide or type of nucleotide, in the case shown, a labeled A. In particular, the labeled A is repeatedly sampled, but not incorporated, as the next added base should be a T. However, because of the multiple sampling of labeled A's, the resulting signal illustrated in an exemplary signal plat, below the schematic of the reaction, can appear more like a prolonged retention time signal associated with an actual incorporation event, e.g., as shown subsequently for the ultimately incorporated T, again as schematically illustrated in the plot beneath the illustration of the reaction. Although shown as only As and Ts within the reaction environment, it will be appreciated that even in preferred situations where all bases will be present, that the probability of a given, labeled base being repeatedly sampled by the enzyme, remains high, even if one does not account for repeated sampling of the identical proximal base. In particular, if one assumes instantaneous diffusion of a given nucleotide away from the complex following incorrect sampling, and perfect nucleotide distribution of all nucleotides within the reaction mix, the probability of a duplicative sampling of the same type of nucleotide in the reaction would be 25%. As alluded to, however, it would be expected that some amount of repeated sampling of the identical nucleotide would occur, especially where the relative concentration of other nucleotides in the reaction mixture is low.

In accordance with the invention, however, the reaction mixture includes unlabeled and unincorporatable bases that compete for the nonspecific interaction with the labeled bases. As such, the probability of a given type of labeled base being repeatedly sampled will be reduced as a result of this competition. Further, because these unlabeled nucleotides will neither be incorporated nor detectable, they will have no impact on the incorporation events, other than to modulate their frequency. Accordingly, one can adjust the concentration of these competitors to best suit the desired applications, e.g., reduce redundant sampling, etc.

Figure 3:
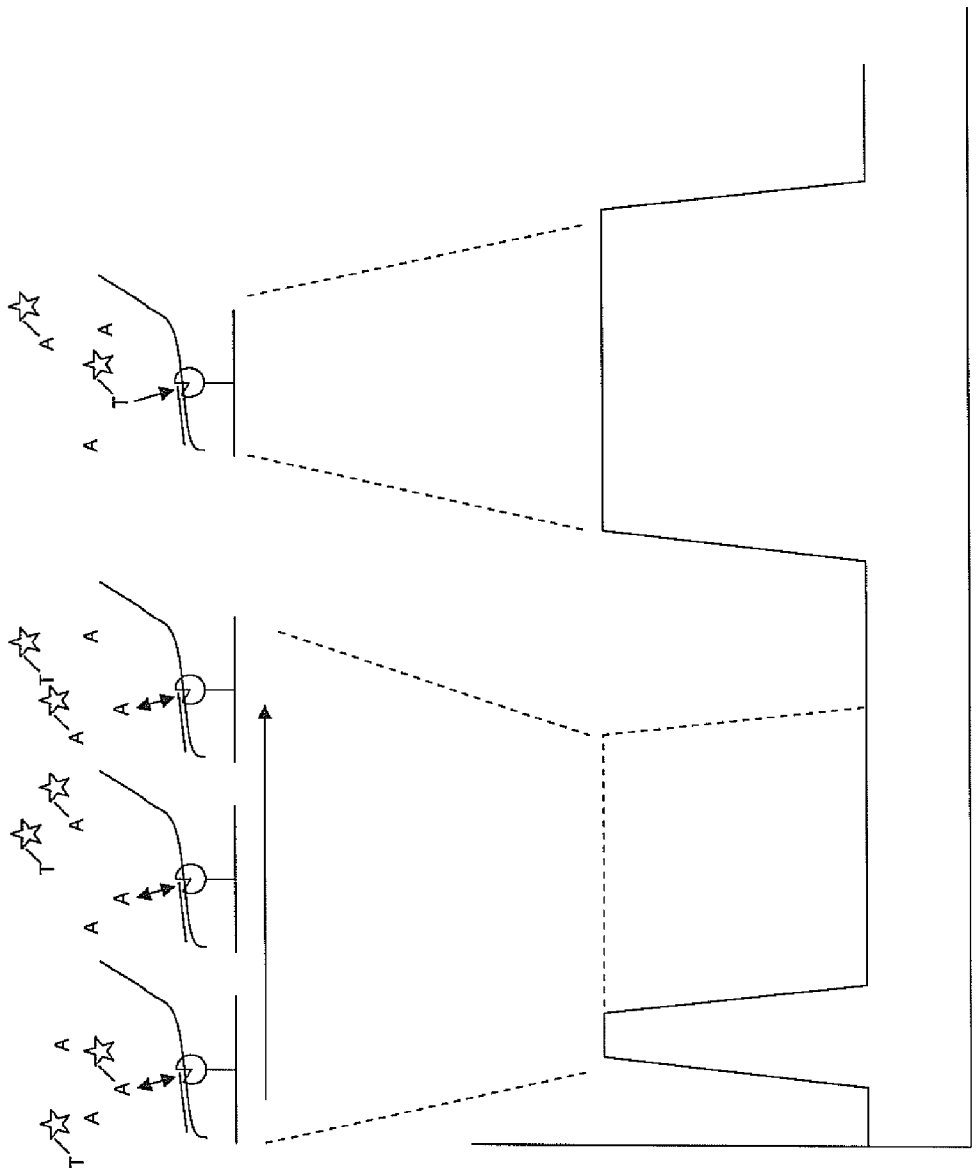
FIG. 3 schematically illustrates nucleic acid synthesis using unincorporatable, unlabeled competitive nucleotide substrates of the invention.

This is schematically illustrated in FIG. 3, which illustrates an identical set of reaction events as shown in FIG. 2, but wherein undetectable competitive nucleotide analogs are used in conjunction with the labeled nucleotides. In particular, the sampling of the fluorescent nucleotide analog (illustrated as an A with a resulting signal profile shown by the solid plot), is interspersed by the sampling of undetectable nucleotide analogs (also As, and shown as a dashed line, although no signal would actually occur). Accordingly, even if the polymerase repeatedly samples the same type of nucleotide analog, the presence of competitive analogs will separate any signal events from each other and render them distinguishable from actual incorporation events.

Although described and illustrated with reference to methods where multiple different types of nucleotide analogs are present at the same time, e.g., A, G, T, C, and/or U, as well as their unincorporatable counterpart analogs, i.e., the unincorporatable analog of the labeled and incorporatable A, G, T, C, and/or U analog, respectively, it will be appreciated that the methods of the invention are also applicable to systems in which single nucleotide analogs are being interrogated in distinct steps, e.g., where a polymerization complex is interrogated or contacted with only one type of nucleotide analog at a time, i.e., bearing one type of nucleobase (adenine, guanine, thymine, cytosine, uracil, inosine and the like).

In such cases, it will be appreciated that the unincorporatable counterpart nucleotide analog may likewise be present as the only type of unincorporatable analog. Alternatively, in some cases, it may be advantageous to provide a plurality of different types of unincorporatable analogs while providing only a single type of incorporatable analog. Conversely, there may also be situations in which one desires to modulate sampling of only a certain type of analog. In such cases, while multiple different types of incorporatable analogs may be present in the reaction mixture, only a single type of unincorporatable analog, or less than all four types of unincorporatable analogs, may be present in the mixture.

In addition to providing the ability to modulate the rate of incorporation of labeled analogs, it will also be appreciated that the use of unincorporatable analogs of the invention also provides the ability to maintain elevated concentrations of labeled analogs even in the face of improving kinetics of engineered polymerases. In particular, improvements in engineered polymerases useful in the preferred sequencing applications described herein, have resulted in substantially reduced Km values for the enzymes relative to the labeled analogs. As a result, optimal reaction conditions for such enzymes result in lower concentrations of labeled analogs that could potentially result in reaction limiting amounts of such analogs, thus potentially reducing overall ability to synthesize, and consequently obtain long individual molecule read lengths of nucleic acid sequences. By providing competitive, unincorporatable analogs along with the incorporatable analogs, one can effectively mediate the effects of higher analog concentration through competition with unlabeled, unincorporatable nucleotide analogs.

In addition to the foregoing, and without being bound to any particular theory of operation, it is also believed that processivity of the polymerase, as well as its resistance to certain negative photoinduced damage events, may be improved when the polymerase has bound in its active site a nucleotide or nucleotide analog in preparation for incorporation in an extension reaction. For example, it is believed that for certain polymerases, lack of a nucleotide within its active site provides an increased opportunity for the 3' end of the nascent strand to transition into the exonuclease function of the polymerase, even when exonuclease activity has been engineered out of the enzyme. In the context of the sequencing methods described herein, this could potentially lead to pauses during processive synthesis or an increased possibility of dissociation of the overall complex. In such cases, the presence of the competitive unincorporatable nucleotides of the invention provides active site coupling analogs without consequent incorporation.

In an alternative or additional configuration, the nucleotide based competitive reagent compositions of the invention may be directly employed in identifying sequence elements, despite not being incorporated in a nascent nucleic acid strand. In particular, The unincorporatable nucleotide analogs of the invention, while not being incorporatable, may be nonetheless capable of specifically associated with the polymerase enzyme. That is, the polymerase will sample the unincorporatable nucleotides, retaining them within the active site for a greater length of time than nucleotides that are not complementary to the position in the template nucleic acid, and release them when they cannot be incorporated. By providing different types of nucleotide or nucleoside analogs, e.g., mimetic of A, G, T C, and/or U, bearing distinguishable labels, e.g., spectrally resolvable fluorophores or other labeling groups, one can monitor the sampling of these nucleotides as an indication of the nucleotide that is next to be incorporated. For example, one may provide labeled, unincorporatable nucleotide analogs at concentrations in excess of incorporatable nucltides, e.g., 2×, 5× or even 10× or greater. Each incorporation of an incorporatable nucleotide will, by virtue of the excess concentration, be preceded by repeated sampling events of the unincorporatable nucleotides, which will each carry its associated signal event. The incorporatable nucleotides may then either bear no label, or preferably, bear a label that is distinguishable from the unincorporatable nucleotides, so as to mark the termination of the sampling of a given base and proceeding onto the next base in the sequence. In such cases, it may be desirable to label all incorporatable nucleotides with a single type of fluorophore, i.e., indistinguishable from the label groups on the other types of incorporatable nuclotides present, but distinguishable from all of the unincorporatable nucleotides.

Figure 4:
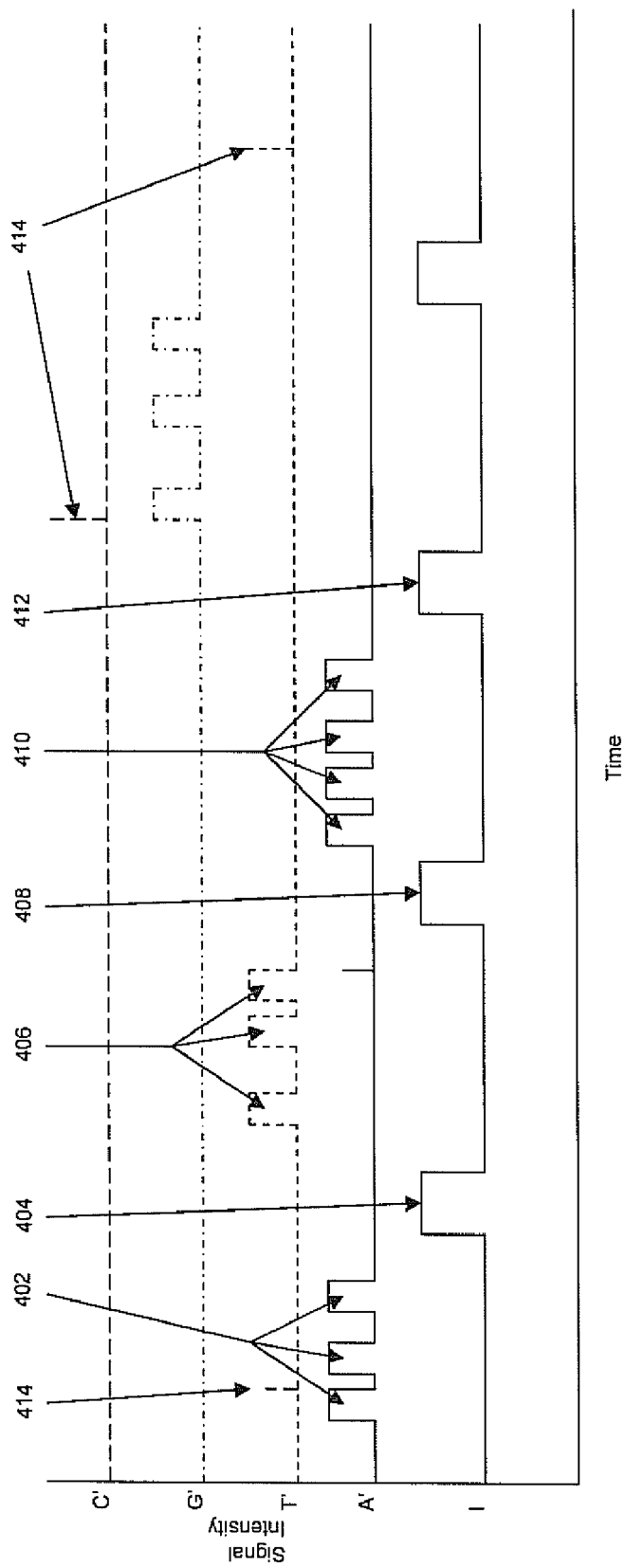
FIG. 4 shows a schematic signal profile of a sampling based sequence determination process using the compositions of the invention.

The signal detection for the foregoing process is schematically illustrated in FIG. 4. In particular, FIG. 4 shows a schematic illustration of a set of signal traces from a single molecule sequence by incorporation reaction. As shown, the plot shows five signal traces. One for each type of differentially labeled unincoporatable nucleotide analog (indicated as A', T', G' and C', as well as a trace for the signal associated with the type of label coupled to the incorporatable nucleotide (labeled as "I"). As shown, repeated sampling of the cognate unincorporatable nucleotide analog, e.g., A', provides an iterative set of signal events 402, followed by a signal 404 on the I trace indicating conclusion of the incorporation event. This pattern is repeated for the next base to be incorporated (indicated by iterative signals 406 in the T' trace, followed again by the incorporation signal 408, in the I trace, and again by the iterative sampling signal 410 in the A' trace followed by the incorporation signal 412 in the I trace. Because these unincorporatable nucleotides are mimetic of the base to be incorporated, they possess a longer retention time in the active site than the analog that is not complementary to the next base in the template, and as such, provide a signal profile that is distinguishable from random, incorrect sampling, e.g., as indicated by transient signal events 414. Such iterative sampling may include two, three, four, five, ten or greater than ten signal events for each incorporation.

As noted above, the competitive reagents used are going to be non-reactive in the reaction of interest. In preferred aspects, and without being bound to any particular theory of operation, the competitive compounds may possess structures similar to nucleotides or portions thereof, such that they can competitively interact with the reaction of interest, e.g., through association with the polymerase active site. By way of example, such structures may comprise a polyphosphate component, e.g., a pyrophosphate, triphosphate, tetraphosphate, pentaphosphate, or longer phosphate chain, so that the compound mimics one or more of a nucleotide or the product of a polymerase mediated incorporation reaction, which is capable of competitively interacting with the polymerase, relative to the nucleotide analogs.

In certain preferred cases, additional components may be coupled to the polyphosphate component that mimic other portions of the nucleotide or nucleotide analog. By way of example, the polyphosphate component may be coupled to a cyclic and/or aromatic component that may structurally mimic the nucleoside component in its interaction with the polymerase. Such structures are generally illustrated by the following structure:

where P is a phosphate or phosphonate group, n is an integer from 1 to 6, and A includes a cycloalkyl or aryl group, a carbohydrate group, or the like.

In the case of nucleotide analogs used in analytical primer extension reactions, e.g., in nucleic acid sequence analysis, such nucleotide analogs will be unincorporatable in such primer extension reaction by the polymerase used. Further, in preferred aspects, such unincorporatable analogs will typically still be capable of interaction with the polymerase, e.g., active site binding, but will be unable to be incorporated in a primer extension reaction. In preferred aspects, this is accomplished by providing nucleotide analogs that possess unhydrolyzable groups within the phosphate chain, such that the phosphoester linkage between the analog and the primer strand, cannot be formed, as mediated by the polymerase. One particularly effective approach to producing an unincorporatable nucleotide analog includes replacing the phosphoester linkage between the alpha and beta phosphate of a nucleoside polyphosphate with a nonhydrolyzable linkage.

One example of such an analog is illustrated below, where tie oxygen group between the alpha and beta phosphate groups is replaced with an unhydrolyzable linkage, such as the illustrated amino group.

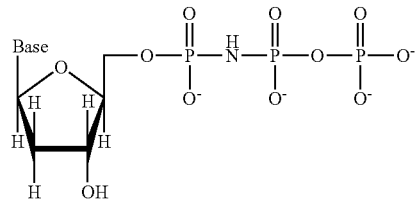

Although illustrated as an amino linkage, it will be appreciated that a variety of other linkages may be used between the alpha and beta phosphates, e.g., an amino, methyl, thio, or other linkages not hydrolyzed by polymerase activity. Additionally, although illustrated as including three phosphate groups analogous to a nucleoside triphosphate, it will be appreciated that other polyphosphate configurations may be employed in the invention, including, for example, tetraphosphate analogs, pentaphosphate analogs, hexaphosphate analogs, and the like.

Thus, the structures employed in certain preferred aspects of the invention may generally be described with reference to the following structure:

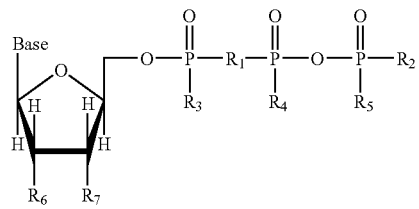

where $R_1$ comprises a linking group that is non-hydrolyzable by the polymerase enzyme being used. Particularly preferred linkages include amino linkages, alkyl linkages, e.g., methyl, and thio linkages. While $R_2$ may comprise oxygen, in some preferred aspects, it will include additional phosphate groups, e.g., mono-, di-, or triphosphate groups coupled to the gamma phosphate group. Alternatively or additionally, the $R_2$ group may include, in addition to or instead of additional phosphate groups, labeling functionalities that provide for the detection of the competitive substrates, but still permit its distinguishing from the incorporatable nucleotides. In other aspects, the $R_2$ group (or corresponding groups on other structures described herein, i.e., group $R_9$ discussed with reference to other compounds, below), may include moieties that provide other functionalities to the reaction system other than as a labeling group. For example, $R_2$ may comprise an agent that reduces the potential for photodamaging effects on a polymerase enzyme, either coupled directly to the terminal phosphate group, or through a linking group.

Such moieties include, for example, triplet state quencher moieties that, when bound in the active site of the polymerase, may function to reduce the level of triplet state fluorophores within or near the active site of the enzyme. A variety of reducing agents or anti-fade agents may be used as triplet state quenchers, including without limitation ascorbic acid, dithiothreitol (DTT), mercaptoethylamine (MEA), β-mercaptoethanol (BME), n-propyl gallate, p-phenylenediamene (PPD), hydroquinone, sodium azide ($NaN_3$), diazobicyclooctane (DABCO), cyclooctatetraene (COT), as well as commercially available anti fade agents, such as Fluoroguard (available from BioRad Laboratories, Inc., Hercules, Calif.), Citifluor antifadants (Citifluor, Ltd., London, UK), ProLong, SlowFade, SlowFade Light (Invitrogen/Molecular Probes, Eugene, Oreg.), and 3-nitrobenzoic acid (NBA). As will be appreciated, in the context of the invention, the foregoing agents may optionally or additionally be included separately from the dye labeled compounds, e.g., as reaction mixture additives. Alternatively or additionally, oxygen scavenging groups may be provided to remove radical oxygen species in or around the enzyme. Examples of oxygen scavengers include, for example, lycopene, α, β, and γ-carotene and their analogs, antheraxanthin, astaxanthin, canthaxanthin, (See, e.g., Carcinogenesis vol. 18 no. 1 pp. 89-92, 1997), neurosporene, rhodopin, bixin, norbixin, zeaxanthin, lutein, bilirubin, biliverdin, and tocopherols (See, e.g., Biochem Soc Trans. 1990 December; 18(6): 1054-6 ref.) as well as polyene dialdehydes (Carcinogenesis vol. 18 no. 1 pp. 89-92, 1997) melatonin, vitamins E (α-tocopheryl succinate and its analogs) and $B_6$ (pyridoxine1 and its derivatives). Other chemical oxygen scavengers are also available, e.g., hydrazine ($N_2H_4$), sodium sulfite ($Na_2SO_3$), hydroxylamine, glutathione, and N-acetylcysteine, histidine, tryptophan, and the like. In addition to the foregoing, in many cases, the amount of singlet oxygen quenchers or scavengers may be reduced or eliminated by physically excluding oxygen from the reaction of interest by, e.g., degassing reagents, perfusion with inert gases, or the like. In addition to the foregoing, as an additional or alternative to the foregoing compounds, anti-oxidants may also be provided in the reaction mixture, including, e.g., Trolox and its analogs U-78715F and WIN62079, a soluble form of vitamin E, having a carboxyl substitution, or in the case of analogs, other substitutions, in place of the vitamin E phytyl side chain, ascorbic acid (or ascorbate), butylated hydroxytoluene (BTH), and the like.

Use of such triplet state quenchers or oxygen scavengers as a functional moiety of a nucleotide analogs has been previously described in Provisional U.S. patent application Ser. No. 61/026,992, filed Feb. 7, 2008, and incorporated herein by reference in its entirety for all purposes.

The remaining substituents, e.g., $R_3$-$R_7$ are independently selected from groups that are known in the art to be incorporatable at these positions in nucleotide analogs for various applications. For example, $R_3$-$R_5$ may generally be independently selected from O, $BH_3$, and S. In addition, while $R_6$ and $R_7$ are preferably H and OH, respectively, it will be appreciated that for different applications, they may each be independently selected from H and OH.

Typically, except for structural alterations used to render them unincorporatable, and a missing or distinguishable label, the competitive substrates of the invention will often mirror the structure of the nucleotide analogs with which they are intended to compete. For example, typically all four standard nucleobases will be represented among the competitive substrates within the reaction mixture, i.e., Adenine, Guanine, Thymine, Cytosine, and/or Uracil, at the same or similar ratios to each other, as for the incorporatable nucleotide analogs. Further, as noted above, the competitive substrates will preferably lack any labeling groups, such as fluorescent dyes, or the like, in order to avoid any contribution of such labels to signal noise levels within the reaction system. However, in the event that labeling is desired to monitor the interaction between the reaction complex and the competitive substrates, one would typically employ a labeling group that is distinguishable from all of the labels employed on the incorporatable nucleotides. In particular, one may employ fluorescent labels having distinct excitation or emission spectra, so as to permit their differential detection through either differential illumination or differential signal direction.

In other aspects, non-nucleotide compounds may be employed as the competitive reagents to the incorporatable nucleotides. Examples of such non-nucleotide or other competitive reagents include compounds that, with respect to binding within the active site of a polymerase, are mimetics of nucleotides or nucleotide analogs. Such compounds will typically comprise pyrophosphate or polyphosphate compounds. These pyrophosphate and/or polyphosphate compounds are typically capable of binding to the catalytic center of the polymerase mimicking the polymerization reaction product and thus competing with labeled nucleotide analogs in the active site binding of such nucleotides. As these compounds are not nucleotides, they would not yield any consequent incorporation event.

The polyphosphate compounds of the invention will typically comprise one of the following structures:

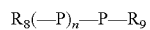

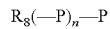

where P is selected from a substituted or unsubstituted phosphate or phosphonate group, where such phosphate groups may be joined by phosphodiester linkages, amine groups, sulfur groups, alkyl groups, or the like as discussed elsewhere herein, $R_8$ comprises a substituted or unsubstituted cycloalkyl or aryl group, including, e.g., heterocyclic, bicycloalkyl, and carbohydrate groups, such as ribosyl or glucosyl groups, which are optionally coupled through alkyl linker groups, and $R_9$, when present, may include a detectable labeling group, e.g., an optical or electrochemically detectable label group, such as a fluorophore or fluorescent or luminescent compound or particle; and n is an integer from 1 to 6, and further provided that such compounds are not incorporatable by a nucleic acid polymerase into a nascent nucleic acid strand.

One particularly exemplary compound of the foregoing structure includes a cyclobenzyl group linked to a pentaphosphate compound (also referred to herein as Cbz-x-5P) of the structure:

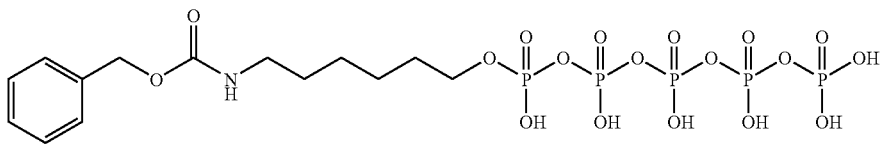

As noted previously, fewer or more phosphates may be included within the phosphate chain portion of the compound. Furthermore, it should be noted that although this substrate is not incorporated, it may function as a substrate in a base excision. However, this activity is negligible compared to sequencing/base incorporation and therefore does not interfere with its use in the invention.

The relative concentration of the competitive substrates to the incorporatable substrates, within a reaction mixture may generally be varied in accordance with a desired application. In particular, because the concentration of the competitive substrates affects the interactions of the complex with the incorporatable nucleotides, one can modulate those interactions by altering the ratios between incorporatable nucleotides and competitive substrates. In typical applications, however, the relative molar concentration of competitive substrate will range from about 0.5× to about 10×, 20× or greater of the concentration of the actual substrates (or incorporatable nucleotide analogs). Thus, the concentration ratio of unincorporatable nucleotide analogs to incorporatable nucleotide analogs will typically range from a lower ratio of from about 0.1:1, 0.2:1 0.5:1 and 1:1, to an upper ratio of about 2:1, 3:1, 5:1, 10:1 or even 20:1, with each iteration of the foregoing being encompassed in the disclosure hereof.

EXAMPLES

Polymerase mediated primer extension reactions were carried out in varying concentrations of a nucleotide mimetic compound to measure the competitive impact of such compounds on nucleotide incorporation by polymerases. Nucleotide incorporation was measured based upon the elongation rate of the polymerization reaction in the presence of varying concentrations of the competitive compound, as determined from the change in synthesis product size, by agarose gel electrophoresis.

A DNA primer extension reaction was carried out using a short circular template sequence using an exonuclease deficient modified phi29 DNA polymerase in the presence of 10 µM of dTTP, 10 µM dCTP, 5 µM Alexa Fluor® 660 labeled deoxyadenosine hexaphosphate (dA6P), and 5 µM Alexa Fluor® labeled deoxyguonosine hexaphosphate (dG6P), where the fluorescent label was coupled to the terminal phosphate. The reaction buffer was 50 mM ACES at pH 7.1, with 75 mM potassium acetate and 1.5 mM $MnCl_2$. Different reactions were carried out in the absence of Cbz-x-5P (lane 1), or in the presence of 60 µM (lane 2), 125 µM (lane 3) and 250 µM Cbz-x-5P (lane 4). A molecular weight standard was also run (shown in lane 5).

Figure 5:
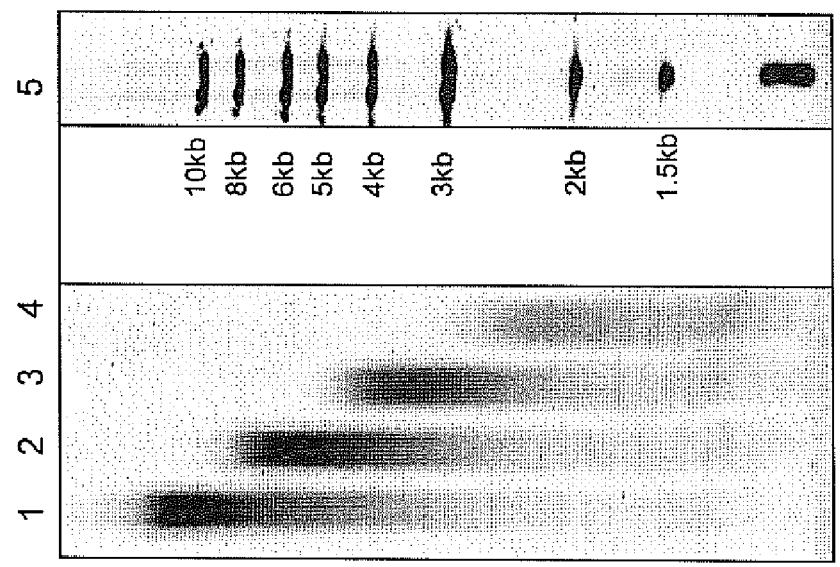
FIG. 5 shows an agarose gel of template dependent, polymerase mediated nucleic acid extension products in the presence of varying concentrations of competitive polymerase reagents.

The extension reaction products were then separated on an agarose gel and are shown in FIG. 5. As can be seen, increased concentration of the competitive compound yields a reduction in the size of the extension product illustrating competitive inhibition of the overall extension reaction and slowing of the overall extension rate of the polymerase.

Figure 6:
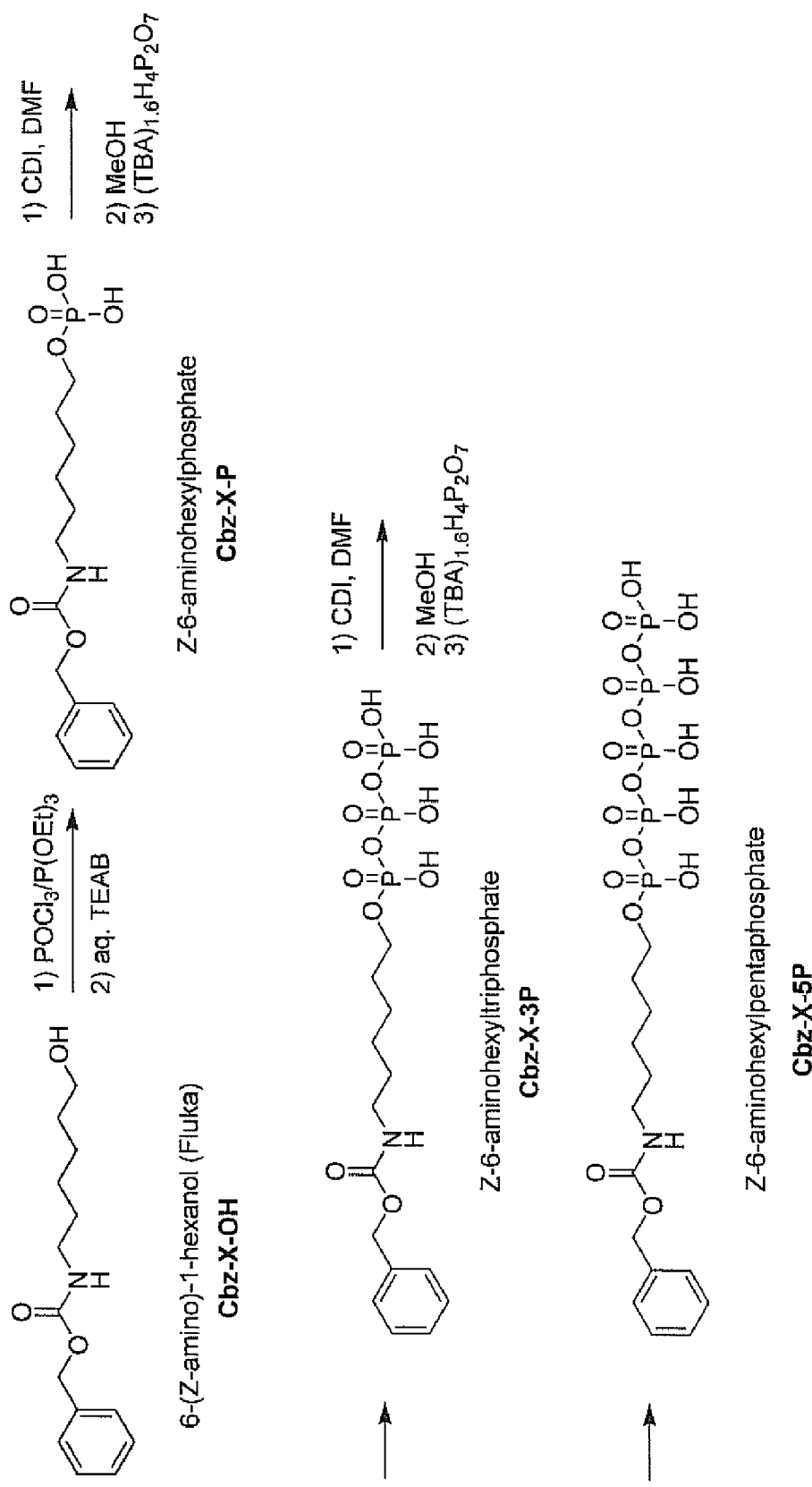
FIG. 6 illustrates synthesis of the unincorporatable competitive polymerase reagent Cbz-x-5P.

Synthesis of Z-6-aminohexylpentaphosphate (Cbz-X-5P) was prepared from commercial 6-(Z-amino)-1-hexanol (Fluka) in a multi-step synthesis. In the first step, 6-(Z-amino)-1-hexanol was converted to Z-6-aminohexylphosphate using phosphorous oxychloride and aqueous work-up. The monophosphate was activated with CDI in anhydrous DMF, the excess of CDI was decomposed with methanol, and the resulting intermediate was treated with commercial tributylammonium pyrophosphate (Sigma) to yield Z-6-aminohexyltriphosphate (Cbz-X-3P). In a similar procedure (CDI, methanol, pyrophosphate), the triphosphate was converted to the final Z-6-aminohexylpentaphosphate (Cbz-X-5P). The product was purified by reverse phase HPLC followed by ion-exchange chromatography. This synthetic scheme is further illustrated in FIG. 6.

Although described in some detail for purposes of illustration, it will be readily appreciated that a number of variations known or appreciated by those of skill in the art may be practiced within the scope of present invention. All terms used herein are intended to have their ordinary meaning unless an alternative definition is expressly provided or is clear from the context used therein. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A composition, comprising:
    a complex comprising a nucleic acid polymerase, a template sequence and a primer sequence complementary to at least a portion of the template sequence;
    at least a first type of incorporatable labeled nucleotide analog; and
    at least a first type of unincorporatable nucleotide analog, said unincorporatable nucleotide analog being unlabeled, wherein the unincorporatable nucleotide analogs comprise an unhydrolyzable link between alpha and beta phosphate groups that is unhydrolyzable by the polymerase enzyme.

2. The composition of claim 1, wherein the unincorporatable nucleotide analog comprises a polyphosphate compound.

3. The composition of claim 1, wherein the competitive polymerase reagent comprises an unincorporatable nucleotide analog.

4. The composition of claim 1, further comprising a plurality of types of incorporatable labeled nucleotides analogs.

5. The composition of claim 4, further comprising a plurality of types of unincorporatable nucleotide analogs.

6. The composition of claim 1, wherein the unhydrolyzable link between the alpha and beta phosphate groups is selected from amino, thio, or alkyl.

7. The composition of claim 1, wherein the unincorporatable nucleotide analog is present at a concentration ratio to the labeled incorporatable nucleotide analogs of from about 0.1:1 to about 20:1.

8. The composition of claim 1, wherein the complex is immobilized upon a solid support.

9. The composition of claim 8, wherein the solid support comprises a transparent substrate.

10. The composition of claim 8, wherein the complex is immobilized upon a solid support such that the complex is individually optically resolvable.

11. The composition of claim 8, wherein the complex is immobilized within an optically confined structure.

12. The composition of claim 1, wherein the unincorporatable nucleotide analog further comprises a triplet state quencher moiety coupled to the unincorporatable nucleotide analog.

13. The composition of claim 2, wherein the unincorporatable nucleotide analog comprises a group coupled to the polyphosphate group, selected from a cycloalkyl group, an aryl group; and a carbohydrate.

14. A method of determining nucleotide sequence information from a target nucleic acid sequence, comprising:
    providing the composition of claim 1, wherein the nucleic acid polymerase is capable of extending the primer sequence in a target sequence dependent manner;
    contacting the complex with a mixture of labeled incorporatable nucleotide analogs and at least a first unincorporatable nucleotide analog reagent that is unlabeled, wherein the unincorporatable nucleotide analogs comprise an unhydrolyzable link between an alpha and beta phosphate groups that is unhydrolyzable by the polymerase enzyme; and
    detecting target dependent incorporation of an incorporatable nucleotide analog to identify a nucleotide in the target nucleic acid sequence.

15. The method of claim 14, wherein, the unincorporatable nucleotide analog comprises a polyphosphate chain.

16. The method of claim 15, wherein the polyphosphate chain comprises from 2 to 7 phosphate groups.

17. The method of claim 14, wherein the unincorporatable nucleotide analog comprises an unincorporatable nucleotide analog.

18. The method of claim 14, wherein the mixture of labeled incorporatable nucleotide analogs comprises a plurality of different types of labeled incorporatable nucleotide analogs and a plurality of different types of unincorporatable nucleotide analogs.

19. The method of claim 14, wherein a ratio of labeled incorporatable nucleotide analogs to unincorporatable nucleotide analog reagent in the mixture is from about 0.1:1 to about 20:1.

20. The method of claim 14, comprising providing the complex in an individually optically resolvable configuration, and optically detecting incorporation of a labeled nucleotide analog in a primer extension reaction by the polymerase enzyme in the complex.

21. The method of claim 14, wherein the unincorporatable nucleotide analog comprises an aryl or cycloalkyl group linked to a polyphosphate group.

\* \* \* \* \*